(12) United States Patent
Cope

(10) Patent No.: US 11,369,680 B2
(45) Date of Patent: Jun. 28, 2022

(54) COMPOUNDS AND COMPOSITIONS FOR TREATING LEISHMANIASIS AND METHODS OF DIAGNOSIS AND TREATING USING SAME

(71) Applicant: Navidea Biopharmaceuticals, Inc., Dublin, OH (US)

(72) Inventor: Frederick O. Cope, Dublin, OH (US)

(73) Assignee: Navidea Biopharmaceuticals, Inc., Dublin, OH (US)

( * ) Notice: Subject to any disclaimer, the term of this patent is extended or adjusted under 35 U.S.C. 154(b) by 0 days.

(21) Appl. No.: 15/729,633

(22) Filed: Oct. 10, 2017

(65) Prior Publication Data

US 2018/0099048 A1  Apr. 12, 2018

Related U.S. Application Data

(60) Provisional application No. 62/405,713, filed on Oct. 7, 2016.

(51) Int. Cl.

| *A61K 39/395* | (2006.01) |
|---|---|
| *A61K 47/26* | (2006.01) |
| *A61K 51/04* | (2006.01) |
| *A61K 51/06* | (2006.01) |
| *A61K 47/61* | (2017.01) |
| *A61K 47/54* | (2017.01) |
| *A61K 49/00* | (2006.01) |
| *A61P 33/02* | (2006.01) |
| *C07K 16/28* | (2006.01) |

(52) U.S. Cl.
CPC ........ *A61K 39/39566* (2013.01); *A61K 47/26* (2013.01); *A61K 47/549* (2017.08); *A61K 47/61* (2017.08); *A61K 49/0032* (2013.01); *A61K 49/0041* (2013.01); *A61K 49/0054* (2013.01); *A61K 51/0491* (2013.01); *A61K 51/0497* (2013.01); *A61K 51/065* (2013.01); *A61P 33/02* (2018.01); *C07K 16/2896* (2013.01)

(58) Field of Classification Search
CPC .. A61K 39/39566; A61K 47/26; A61K 47/61; A61K 47/549; A61K 49/0032; A61K 49/0054; A61K 49/0041; A61K 51/0491; A61K 51/0497; A61K 51/065; A61P 33/02
USPC ......................................................... 514/59
See application file for complete search history.

(56) References Cited

U.S. PATENT DOCUMENTS

| 2009/0311182 A1* | 12/2009 | Wang ................. A61K 49/0002 424/9.1 |
| 2011/0268804 A1* | 11/2011 | Shi ......................... A61K 39/00 424/489 |
| 2017/0209584 A1 | 7/2017 | Schlesinger et al. |
| 2018/0099048 A1 | 4/2018 | Cope |

FOREIGN PATENT DOCUMENTS

| WO | 2015013341 A1 | 1/2015 |
| WO | 2016011415 A2 | 1/2016 |
| WO | 2016011419 A1 | 1/2016 |
| WO | 2016118188 A1 | 7/2016 |
| WO | 2018068059 A1 | 4/2018 |

OTHER PUBLICATIONS

Smith et al, Journal of Inflammation, 2004, 1(3), pp. 1-12.*
Vergnolle, Mem. Inst. Oswaldo Cruz, Rio de Janeiro, 2005, 100 (suppl. 1), pp. 173-176.*
The Merck Manual, 1992, pp. 77-85.*
Dumitriu, S. Polysaccharides in Medicinal Applications, Marcel Dekker, N.Y., 1996, Chapt. 16, Medical Applications of Dextran and Its Derivatives, pp. 505-514.*
Pustylnikov et al, Journal of Pharm. Pharm. Sci., 2014, 17(3), 371-392.*

\* cited by examiner

*Primary Examiner* — Ganapathy Krishnan
(74) *Attorney, Agent, or Firm* — Sean Solberg

(57) ABSTRACT

Compositions and methods of using these compositions that can include a targeting moiety and a therapeutic agent are described herein. These compositions can be used for treating inflammatory diseases, such as parasitic diseases that result in cutaneous lesions. For example, and without limitation, such an parasitic disease can be leishmaniasis.

11 Claims, 8 Drawing Sheets

Red: Tilmanocept-Cy3
Green: GFP-M. tuberculosis
Yellow: Tilmanocept-Cy3 & M. tuber Scheme 1: Synthetic route A for the modification of MAD Scheme 2: Synthetic route B for the modification of MAD Scheme 3: Conjugation of doxorubicin to MAD derivatives Scheme 4: Reaction between a primary amine and the lactone

COMPOUNDS AND COMPOSITIONS FOR TREATING LEISHMANIASIS AND METHODS OF DIAGNOSIS AND TREATING USING SAME

CROSS-REFERENCE TO RELATED APPLICATIONS

This application claims priority to of U.S. Provisional Application No. 62/405,713 filed Oct. 7, 2016, the contents of which is incorporated by reference herein in its entirety.

DETAILED DESCRIPTION

The invention is not limited in its application to the details of construction and the arrangement of components set forth in the following description or illustrated in the following drawings. The invention is capable of other embodiments and of being practiced or of being carried out in various ways.

Among other things, the present invention is directed toward compounds and compositions for targeting dermal macrophages. The present invention also provides methods of making such compounds and compositions. The present invention also provides diagnostic methods and methods of treatment using compounds comprising a dextran-based moiety and methods and methods of treatment using compounds comprising a carbohydrate-based moiety that can be used for treating diseases, such as but not limited to, Leishmaniasis.

Leishmaniasis, (which can also be spelled leishmaniosis), is a disease caused by protozoan parasites of the genus *Leishmania* and spread by the bite of certain types of sandflies. Leishmaniasis can be present in at least three ways: cutaneous, mucocutaneous, or visceral leishmaniasis. The cutaneous form presents with skin ulcers, while the mucocutaneous form presents with ulcers of the skin, mouth, and nose, and the visceral form starts with skin ulcers and then later presents with fever, low red blood cells, and enlarged spleen and liver. Infections in humans can be caused by more than 20 species of *Leishmania*. Risk factors include poverty, malnutrition, deforestation, and urbanization and troops are particularly concerned with exposure. All three of these types can be diagnosed by seeing the parasites under a microscope.

Traditional treatment can be determined by where the disease is acquired, the species of *Leishmania*, and the type of infection. Some traditional medications used for visceral disease include liposomal amphotericin B, a combination of pentavalent antimonials (although almost all infections in India are resistant to pentavalent antimonials) and paromomycin, and miltefosine. For cutaneous disease, traditional medications have included paromomycin, fluconazole, or pentamidine may be effective. All of these medications can be used as therapeutic agents in combination with tilmanocept.

About 12 million people are currently infected with leishmaniasis in some 98 countries. About 2 million new cases and between 20 and 50 thousand deaths occur each year. About 200 million people in Asia, Africa, South and Central America, and southern Europe live in areas where the disease is common. The World Health Organization has expressed considerable interest in medications and therapeutics for treating leishmaniasis. The disease may occur in a number of other animals, including dogs and rodents.

Leishmaniasis can be transmitted by the bite of infected female phlebotomine sandflies which can transmit the protozoa *Leishmania*. The sandflies can inject the infective stage, metacyclic promastigotes, while feeding on a host's blood. Metacyclic promastigotes that reach the puncture wound can be phagocytized by macrophages and can transform into amastigotes. Amastigotes multiply in infected cells and affect different tissues, depending in part on which *Leishmania* species is involved. These differing tissue specificities can cause the differing clinical manifestations of the various forms of leishmaniasis. Sandflies become infected while feeding on infected host blood and ingest macrophages infected with amastigotes. In the sandfly's midgut, the parasites differentiate into promastigotes, which multiply, differentiate into metacyclic promastigotes, and migrate to the proboscis. The genomes of three *Leishmania* species (*L. major, L. infantum,* and *L. braziliensis*) have been sequenced, and this has provided much information about the biology of the parasite. *L. major* is of particular interest as is discussed further herein.

Leishmaniasis occurs in 88 tropical and subtropical countries. About 350 million people live in these areas. The settings in which leishmaniasis is found range from rainforests in Central and South America to deserts in western Asia and the Middle East. It affects as many as 12 million people worldwide, with 1.5-2.0 million new cases each year.

More than 90% of the world's cases of visceral leishmaniasis are in India, Bangladesh, Nepal, Sudan, and Brazil. As of 2010, it caused about 52,000 deaths, down from 87,000 in 1990. Different types of the disease occur in different regions of the world. Cutaneous leishmaniasis is most common in Afghanistan, Algeria, Brazil, Colombia, and Iran, while mucocutaneous leishmaniasis is most common in Bolivia, Brazil, and Peru, and visceral leishmaniasis is most common in Bangladesh, Brazil, Ethiopia, India, and Sudan. Leishmaniasis is found through much of the Americas from northern Argentina to South Texas, though not in Uruguay or Chile, and has recently been shown to be spreading to North Texas. During 2004, an estimated 3,400 troops from the Colombian army, operating in the jungles near the south of the country (in particular around the Meta and Guaviare departments), were infected with leishmaniasis.

Leishmaniasis can be found across much of Asia, and in the Middle East In Kabul, the number of people infected was estimated to be at least 200,000, and in three other towns (Herat, Kandahar, and Mazar-i-Sharif) about 70,000 more occurred, according to WHO figures from 2002.

Leishmaniasis is rarely known in the developed world outside of cases where troops are stationed away from their home countries. Leishmaniasis has been reported by U.S. troops stationed in Saudi Arabia and Iraq since the Gulf War of 1990, including visceral leishmaniasis. In September 2005, the disease was contracted by at least four Dutch marines who were stationed in Mazari Sharif, Afghanistan, and subsequently repatriated for treatment. As such, there are needs for improved treatments for leishmaniasis and tilmanocept as described herein provides unexpectedly improved treatments.

DETAILED DESCRIPTION OF THE DRAWINGS

DEFINITIONS

Figure 1A:
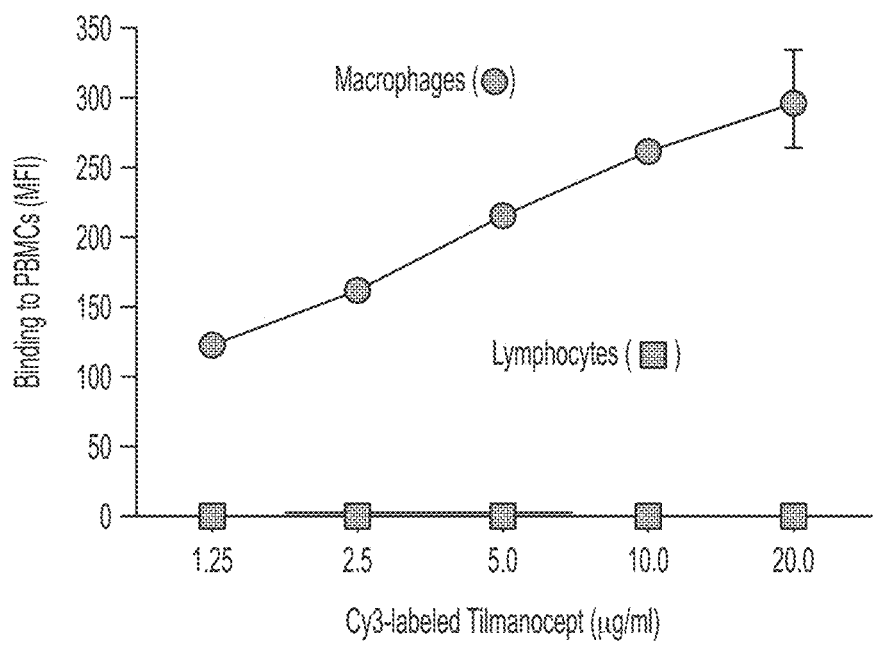
FIGS. 1A, 1B and 1C show a series of images of binding of an example of a macrophage-targeting compositions described herein.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Perkin Elmer Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the identification can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, intradermal administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. CD206), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause unacceptable adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. More than one substituent may be present. Substituents may also be themselves substituted. When substituted, the substituent group is preferably but not limited to $C_1$-$C_4$ alkyl, aryl, heteroaryl, amino, imino, cyano, halogen, alkoxy or hydroxyl. "$C_1$-$C_4$ alkyl" refers to alkyl groups containing one to four carbon atoms.

"Alkenyl" refers to an unsaturated aliphatic hydrocarbon moiety including straight chain and branched chain groups. Alkenyl moieties must contain at least one alkene. "Alkenyl" may be exemplified by groups such as ethenyl, n-propenyl, isopropenyl, n-butenyl and the like. Alkenyl groups may be substituted or unsubstituted. More than one substituent may be present. When substituted, the substituent group is preferably alkyl, halogen or alkoxy. Substituents may also be themselves substituted. Substituents can be placed on the alkene itself and also on the adjacent member atoms or the alkenyl moiety. "$C_2$-$C_4$ alkenyl" refers to alkenyl groups containing two to four carbon atoms.

"Alkynyl" refers to an unsaturated aliphatic hydrocarbon moiety including straight chain and branched chain groups. Alkynyl moieties must contain at least one alkyne. "Alkynyl" may be exemplified by groups such as ethynyl, propynyl, n-butynyl and the like. Alkynyl groups may be substituted or unsubstituted. More than one substituent may be present. When substituted, the substituent group is preferably alkyl, amino, cyano, halogen, alkoxyl or hydroxyl. Substituents may also be themselves substituted. Substituents are not on the alkyne itself but on the adjacent member atoms of the alkynyl moiety. "$C_2$-$C_4$ alkynyl" refers to alkynyl groups containing two to four carbon atoms.

"Acyl" or "carbonyl" refers to the group —C(O)R wherein R is alkyl; alkenyl; alkynyl, aryl, heteroaryl, carbocyclic, heterocarbocyclic; $C_1$-$C_4$ alkyl aryl or $C_1$-$C_4$ alkyl heteroaryl. $C_1$-$C_4$ alkylcarbonyl refers to a group wherein the carbonyl moiety is preceded by an alkyl chain of 1-4 carbon atoms.

"Alkoxy" refers to the group —O—R wherein R is acyl, alkyl alkenyl, alkyl alkynyl, aryl, carbocyclic; heterocarbocyclic; heteroaryl, $C_1$-$C_4$ alkyl aryl or $C_1$-$C_4$ alkyl heteroaryl.

"Amino" refers to the group —NR'R' wherein each R' is, independently, hydrogen, amino, hydroxyl, alkoxyl, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring. The R' groups may themselves be further substituted, in which case the group also known as guanidinyl is specifically contemplated under the term 'amino".

"Aryl" refers to an aromatic carbocyclic group. "Aryl" may be exemplified by phenyl. The aryl group may be substituted or unsubstituted. More than one substituent may be present. Substituents may also be themselves substituted. When substituted, the substituent group is preferably but not limited to heteroaryl, acyl, carboxyl, carbonylamino, nitro, amino, cyano, halogen, or hydroxyl.

"Carboxyl" refers to the group —C(=O)O—$C_1$-$C_4$ alkyl.

"Carbonyl" refers to the group —C(O)R wherein each R is, independently, hydrogen, alkyl, aryl, cycloalkyl; heterocycloalkyl, heteroaryl, $C_1$-$C_4$ alkyl aryl or $C_1$-$C_4$ alkyl heteroaryl.

"Carbonylamino" refers to the group —C(O)NR'R' wherein each R' is, independently, hydrogen, alkyl, aryl, cycloalkyl, heterocycloalkyl, heteroaryl, $C_1$-$C_4$ alkyl aryl or $C_1$-$C_4$ alkyl heteroaryl. The two R' groups may themselves be linked to form a ring.

"$C_1$-$C_4$ alkyl aryl" refers to $C_1$-$C_4$ alkyl groups having an aryl substituent such that the aryl substituent is bonded through an alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through an alkyl group.

"Carbocyclic group" or "cycloalkyl" means a monovalent saturated or unsaturated hydrocarbon ring. Carbocyclic groups are monocyclic, or are fused, spiro, or bridged bicyclic ring systems. Monocyclic carbocyclic groups contain 3 to 10 carbon atoms, preferably 4 to 7 carbon atoms, and more preferably 5 to 6 carbon atoms in the ring. Bicyclic carbocyclic groups contain 8 to 12 carbon atoms, preferably 9 to 10 carbon atoms in the ring. Carbocyclic groups may be substituted or unsubstituted. More than one substituent may be present. Substituents may also themselves be substituted. Preferred carbocyclic groups include cyclopropyl, cyclobutyl, cyclopentyl, cyclohexyl, cyclohexenyl, and cycloheptyl. More preferred carbocyclic groups include cyclopropyl and cyclobutyl. The most preferred carbocyclic group is cyclopropyl. Carbocyclic groups are not aromatic.

"Halogen" refers to fluoro, chloro, bromo or iodo moieties. Preferably, the halogen is fluoro, chloro, or bromo.

"Heteroaryl" or "heteroaromatic" refers to a monocyclic or bicyclic aromatic carbocyclic radical having one or more heteroatoms in the carbocyclic ring. Heteroaryl may be substituted or unsubstituted. More than one substituent may be present. When substituted, the substituents may themselves be substituted. Preferred but non limiting substituents are aryl, $C_1$-$C_4$ alkylaryl, amino, halogen, hydroxy, cyano, nitro, carboxyl, carbonylamino, or $C_1$-$C_4$ alkyl. Preferred heteroaromatic groups include tetrazoyl, triazolyl, thienyl, thiazolyl, purinyl, pyrimidyl, pyridyl, and furanyl. More preferred heteroaromatic groups include benzothiofuranyl; thienyl, furanyl, tetrazoyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 5 to 6 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. More than one substituent may be present. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are not aromatic.

"Hydroxy" or "hydroxyl" means a chemical entity that consists of —OH. Alcohols contain hydroxy groups. Hydroxy groups may be free or protected. An alternative name for hydroxy is hydroxyl.

"Leash/leashes" and "linker/linkers" may be used interchangeably herein. The term "leash" or "leashes" can often be used to refer to attachment moiety used for a targeting moiety, such as mannose. The term "linker" or "linkers" can be used to refer to the attachment moiety used for a therapeutic agent that may incorporate additional propertiesd related to the chemistry of the linker and therapeutic agent and the delivery of the said agent. Although these terms can be used interchangeably herein, their meaning will be clear to the skilled artisan in view of the context with which it is used "Member atom" means a carbon, nitrogen, oxygen or sulfur atom. Member atoms may be substituted up to their normal valence. If substitution is not specified the substituents required for valency are hydrogen.

"Ring" means a collection of member atoms that are cyclic. Rings may be carbocyclic, aromatic, or heterocyclic or heteroaromatic, and may be substituted or unsubstituted, and may be saturated or unsaturated. More than one substituent may be present. Ring junctions with the main chain may be fused or spirocyclic. Rings may be monocyclic or bicyclic. Rings contain at least 3 member atoms and at most 10 member atoms. Monocyclic rings may contain 3 to 7 member atoms and bicyclic rings may contain from 8 to 12 member atoms. Bicyclic rings themselves may be fused or spirocyclic.

"Thioalkyl" refers to the group —S-alkyl.

"Tilmanocept" can refer to an example of a composition described herein comprising a non-radiolabeled precursor of a diagnostic agent. Tilmanocept may be a mannosylaminodextran. It can have a dextran backbone to which a plurality of amino-terminated linkers (—O(CH$_2$)$_3$S(CH$_2$)$_2$NH$_2$) are attached to the core glucose elements. In addition, mannose moieties can be conjugated to amino groups of a number of the linkers, and the chelator diethylenetriamine pentaacetic acid (DTPA) can be conjugated to the amino group of other linkers not containing the mannose. Tilmanocept generally, has a dextran backbone, in which a plurality of the glucose residues comprise an amino-terminated linker:

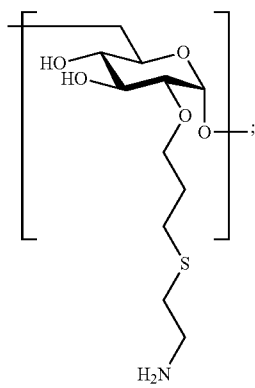

the mannose moieties are conjugated to the amino groups of the linker via an amidine linker:

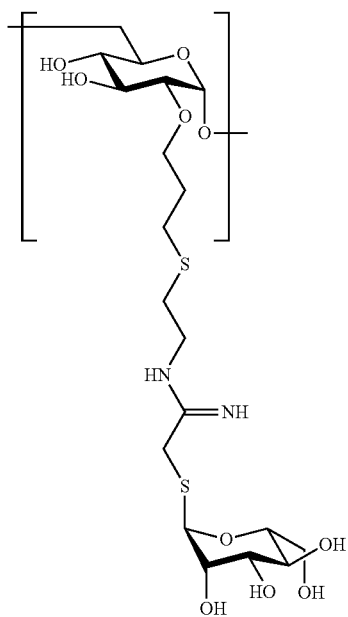

the chelator diethylenetriamine pentaacetic acid (DTPA) is conjugated to the amino groups the linker via an amide linker:

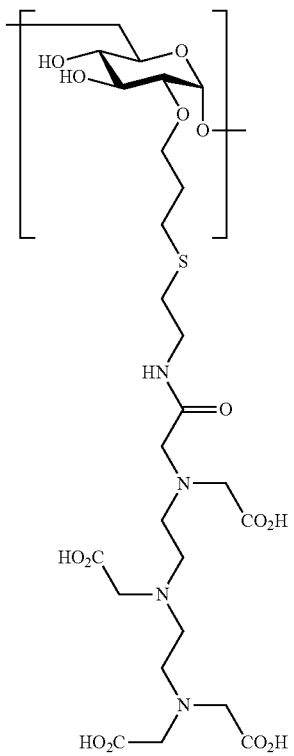

An example of an embodiment described herein can have the chemical name dextran 3-[(2-aminoethyl)thio]propyl 17-carboxy-10,13,16-tris(carboxymethyl)-8-oxo-4-thia-7,10,13,16-tetraazaheptadec-1-yl 3-[[2-[[1-imino-2-(D-mannopyranosylthio)ethyl]amino]ethyl]thio]propyl ether complexes, has the following molecular formula: [C$_6$H$_{10}$O$_5$]$_n$·(C$_{19}$H$_{28}$N$_4$O$_9$S$^{99m}$Tc)$_b$·(C$_{13}$H$_{24}$N$_2$O$_5$S$_2$)$_c$·(C$_5$H$_{11}$NS)$_a$, and contains 3-8 conjugated DTPA molecules; 12-20 conjugated mannose molecules; and 0-17 amine side chains remaining free. Tilmanocept has the following general structure:

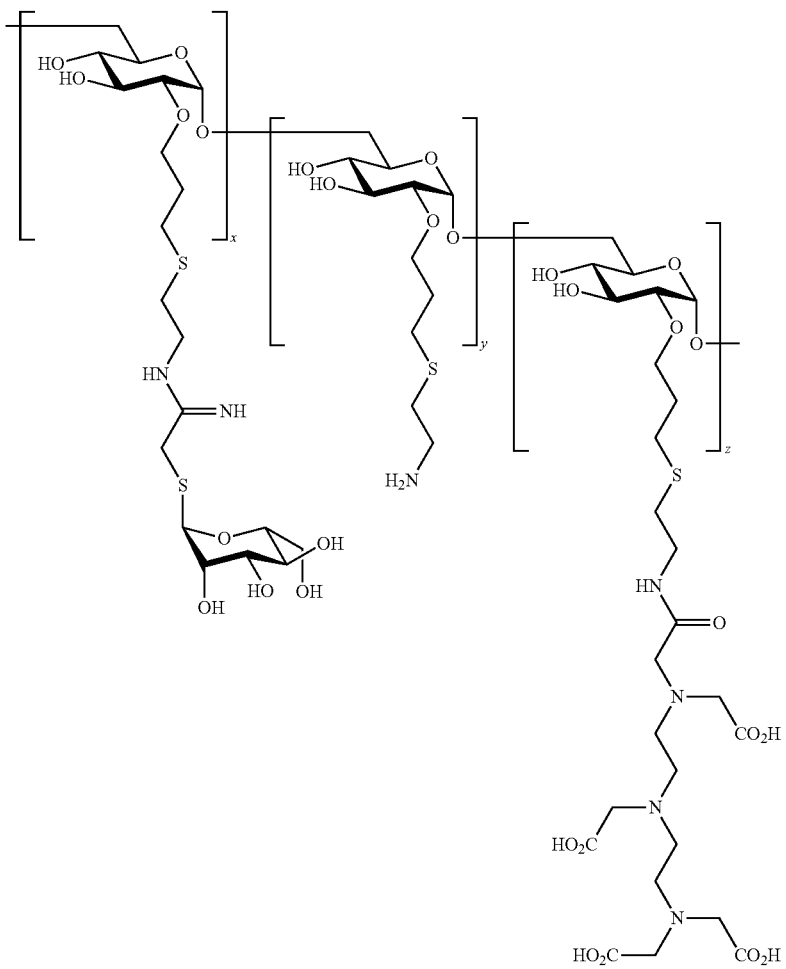

Certain of the glucose moieties may have no attached amino-terminated linker.

"Sulfonyl" refers to the —S(O)$_2$R' group wherein R' is alkoxy, alkyl, aryl, carbocyclic, heterocarbocyclic; heteroaryl, C$_1$-C$_4$ alkyl aryl or C$_1$-C$_4$ alkyl heteroaryl.

"Sulfonylamino" refers to the —S(O)$_2$NR'R' group wherein each R' is independently alkyl, aryl, heteroaryl, C$_1$-C$_4$ alkyl aryl or C$_1$-C$_4$ alkyl heteroaryl.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes may be used for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Compounds

Embodiments of the present invention can employ a carrier construct comprising a polymeric (e.g., carbohydrate) backbone that can comprise a CD206 targeting moiety attached thereto (e.g., mannose) to deliver one or more active pharmaceutical ingredients. Examples of such constructs include mannosylamino dextrans (MAD), which can comprise a dextran backbone having conjugated to glucose residues of the backbone mannose molecules that can be conjugated to other glucose residues of the backbone an active pharmaceutical ingredient. Tilmanocept is a specific example of a MAD. A tilmanocept derivative that is tilmanocept without DTPA conjugated thereto is a further example of a MAD.

In some embodiments, the present invention provides a compound comprising a dextran-based moiety or backbone having one or more CD206 targeting moieties and one or more therapeutic agents attached thereto. The dextran-based moiety generally comprises a dextran backbone similar to that described in U.S. Pat. No. 6,409,990 (the '990 patent), which is incorporated herein by reference in its entirety. Thus, the backbone comprises a plurality of glucose moieties (i.e., residues) primarily linked by α-1,6 glycosidic bonds. Other linkages such as α-1,4 and/or α-1,3 bonds may also be present. Some embodiments may comprise a backbone that is not a dextran backbone. Some embodiments may have a monosaccharide-based backbone that does not comprise dextran. The backbone of a carbohydrate-based carrier molecules described herein can comprise a glycan other than dextran, wherein the glycan comprises a plurality of monosaccharide residues (i.e., sugar residues or modified sugar residues). In certain embodiments, the glycan backbone has sufficient monosaccharide residues, as well as optional groups such as one or more amino acids, polypeptides and/or lipids, to provide a MW of about 1 to about 50 kDa. As would be appreciated by the skilled artisan when considering the disclosure contained herein, when referring to a "dextran" backbone, other monosaccharide residues may be considered to be substituted in compounds described herein. Additional descriptions of carbohydrate-backbone-based carrier molecules used for targeting CD206 are described in PCT application No. US/2017/055211, which is herein incorporated by reference in its entirety. In some embodiments, not every backbone moiety is substituted. In some embodiments, CD206 targeting moieties are attached to between about 10% and about 50% of the glucose residues of the dextran backbone, or between about 20% and about 45% of the glucose residues, or between about 25% and about 40% of the glucose residues. In some embodiments, every three glucose residues may be substituted. In some embodiments, every four glucose residues may be substituted. In some embodiments, every five glucose residues may be substituted. Some embodiments may comprise one mannose positioned on every third glucose residue. Some embodiments may comprise one mannose positioned on every fourth glucose residue. Some embodiments may comprise one mannose positioned on every fifth glucose residue. In some embodiments, the dextran-based moiety is about 50-100 kD. The dextran-based moiety may be at least about 50 kD, at least about 60 kD, at least about 70 kD, at least about 80 kD, or at least about 90 kD. The dextran-based moiety may be less than about 100 kD, less than about 90 kD, less than about 80 kD, less than about 70 kD, or less than about 60 kD. In some embodiments, the dextran backbone has a MW of between about 1 and about 50 kDa, while in other embodiments the dextran backbone can have a MW of between about 5 and about 25 kDa. In embodiments, the dextran backbone can have a MW of between about 8 and about 15 kDa, such as about 10 kDa. While in other embodiments the dextran backbone can have a MW of between about 1 and about 5 kDa, such as about 2 kDa. Certain embodiments of compositions can comprise a backbone that is between about 1 to about 5 kDa, about 1 to about 10 kDa, about 1 to about 15 kDa, about 5 to about 12 kDa, about 5 to about 10 kDa, and ranges therebetween. In some embodiments, a composition may comprise between about 2 to about 7 mannose molecules, about 5 to about 10 mannose molecules, about 10 to about 15 mannose molecules, about 15 to about 20 mannose molecules, about 16 to about 17 mannose molecules, and ranges therebetween. In some embodiments, a backbone may be about 1 to about 3 kDa and may further comprise about 3 to about 7 mannose molecules. In some embodiments, a backbone may be about 10 kDa and may further comprise about 15 to about to about 28, or about 16 to about 17 mannose molecules. In some embodiments, a therapeutic molecule can comprise about 1 to about 5 molecules (e.g., therapeutic agents), about 3 to 10 molecules, about 7 to about 20 molecules, and ranges therebetween An embodiment may comprise a backbone that is about 10 kDa and further comprise about 2 therapeutic agent molecules, wherein the therapeutic agent molecules can comprise doxorubicin, and further comprise about 16 to about 17 mannose molecules. Such a configuration has unexpectedly superior and improved solubility, improved clarity, improved injectability and biodistribution, and can reduce the amount of active drug required to achieve a therapeutic result at a fraction of the free therapeutic agent.

Carrier molecules having smaller MW dextran backbones may be appropriate for instances where the molecule is desired to cross the blood-brain barrier, or when reduced residence time is desired (i.e., the duration of binding to CD206 is reduced). Carrier molecules having larger MW dextran backbones may be appropriate for instances where increased residence time is desired (i.e., the duration of circulation and exposure to CD206 is increased). In certain embodiments, carrier molecules having smaller MW dextran backbones (e.g., about 1 to about 5 kDa) may be employed when more efficient receptor substrates are attached to the dextran backbone (e.g., branched mannose moieties, as described below). More efficient receptor substrates can bind to CD206 for longer durations and/or more effectively, thus allowing for the use of smaller dextran backbones.

In some embodiments, the CD206 targeting moiety is selected from, but not limited to, mannose, fucose, galactose, n-acetylgalactosamine, and n-acetylglucosamine and combinations of these. In some embodiments, the targeting moieties are attached to between about 10% and about 50% of the glucose residues of the dextran backbone, or between about 20% and about 45% of the glucose residues, or between about 25% and about 40% of the glucose residues. (It should be noted that the MWs referenced herein, as well as the number and degree of conjugation of receptor substrates, linkers, and diagnostic/therapeutic moieties attached to the dextran backbone refer to average amounts for a given quantity of carrier molecules, since the synthesis techniques will result in some variability.)

In some embodiments, the one or more CD206 targeting moieties and one or more therapeutic agents (or drugs) and/or detection labels are attached to the dextran-based moiety through a linker. The linker may be attached at from about 50% to about 100% of the backbone moieties or about 70% to about 90%. In embodiments with multiple linkers, the linkers may be the same or different. In some embodiments, the linker is an amino-terminated linker. In some embodiments, the linkers may comprise —O(CH$_2$)$_3$S(CH$_2$)$_2$NH—. In some embodiments, the linker may be a chain of from 1 to 20 member atoms selected from carbon, oxygen, sulfur, nitrogen and phosphorus. The linker may be a straight chain or branched. The linker may also be substituted with one or more substituents including, but not limited to, halo groups, perfluoroalkyl groups, perfluoroalkoxy groups, alkyl groups, such C$_{1-4}$ alkyl, alkenyl groups, such as C$_{1-4}$ alkenyl, alkynyl groups, such as C$_{1-4}$ alkynyl, hydroxy groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocylic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkyl sulfonyl groups, arylsulfonyl groups, —NH—NH$_2$; =N—H =N-alkyl; —SH; —S-alkyl; —NH—C(O)—; —NH—C(=N)— and the like. Other suitable linkers would be known to one of ordinary skill in the art.

In some embodiments, the one or more therapeutic agent is attached via a biodegradable linker. In some embodiments, the biodegradable linker comprises an acid sensitive, such as a hydrazone moiety. The use of an acid sensitive linker enables the drug to be transported into the cell and allows for the release of the drug substantially inside of the cell. In certain embodiments, the linker comprises a biodegradable moiety attached to a linker.

Various other linkers known to those skilled in the art or subsequently discovered may be used in place of (or in addition to) —O(CH$_2$)$_3$S(CH$_2$)$_2$NH$_2$. These include, for example, bifunctional linker groups such as alkylene diamines (H$_2$N—(CH$_2$)$_r$—NH$_2$), where r is from 2 to 12; aminoalcohols (HO—(CH$_2$)$_r$—NH$_2$), where r is from 2 to 12; aminothiols (HS—(CH$_2$)$_r$—NH$_2$), where r is from 2 to 12; amino acids that are optionally carboxy-protected; ethylene and polyethylene glycols (H—(O—CH$_2$—CH$_2$)$_n$—OH, where n is 1-4). Suitable bifunctional diamines include ethylenediamine, 1,3-propanediamine, 1,4-butanediamine, spermidine, 2,4-diaminobutyric acid, lysine, 3,3'-diaminodipropylamine, diaminopropionic acid, N-(2-aminoethyl)-1,3-propanediamine, 2-(4-aminophenyl)ethylamine, and similar compounds. One or more amino acids also can be employed as the bifunctional linker molecule, such as β-alanine, γ-aminobutyric acid or cysteine, or an oligopeptide, such as di- or tri-alanine.

Other bifunctional linkers include:
—NH—(CH$_2$)$_r$—NH—, where r is from 2-5,
—O—(CH$_2$—NH—, where r is from 2-5,
—NH—CH$_2$—C(O)—,
—O—CH$_2$—CH$_2$—O—CH$_2$—CH$_2$—O—,
—NH—NH—C(O)—CH$_2$—,
—NH—C(CH$_3$)$_2$C(O)—,
—S—(CH$_2$)$_r$—C(O)—, where r is from 1-5,
—S—(CH$_2$)$_r$—NH—, where r is from 2-5,
—S—(CH$_2$)$_r$—O—, where r is from 1-5,
—S—(CH$_2$)—CH(NH$_2$)—C(O)—,
—S—(CH$_2$)—CH(COOH)—NH—,
—O—CH$_2$—CH(OH)—CH$_2$—S—CH(CO$_2$H)—NH—,
—O—CH$_2$—CH(OH)—CH$_2$—S—CH(NH$_2$)—C(O)—,
—O—CH$_2$—CH(OH)—CH$_2$—S—CH$_2$—CH$_2$—NH—,
—S—CH$_2$C(O)—NH—CH$_2$—CH—NH—, and
—NH—O—C(O)—CH$_2$—CH$_2$O—P(O$_2$H)—.

The therapeutic agent may be any compound known to be useful for the treatment of a macrophage-mediated disease such as, but not limited to, leishmaniasis. Therapeutic agents include, but are not limited to, chemotherapeutic agents, such as doxorubicin; dexamethasone, drugs with effect on leishmaniasis; anti-infective agents, such as antibiotics (e.g. tetracycline, streptomycin, amphotericin and isoniazid), heavy metals such as antimony (e.g. pentavalent antimonials), anti-virals, anti-fungals, and anti-parasitics; immunological adjuvants; steroids; nucleotides, such as DNA, RNA, RNAi, siRNA, CpG or Poly (I:C); peptides; proteins; or metals such as silver, gallium or gadolinium, paromomycin, miltefosine, fluconazole, pentamide, Meglumine antimoniate, and combinations thereof. A therapeutic agent may comprise an agent that shifts an M2-phenotype macrophage to an alternative phenotype. For example, but without limitation, heavy metals may be incorporated to alter macrophage phenotypes. Therapeutic agents may comprise interferon gamma and/or zoledronic acid and the like that can shift macrophage phenotypes toward a non-M2 phenotype. Therapeutic agents may comprise IL-4, IL-10, TGF-beta, glucocorticoid, IL-1 beta, and/or imidazole quinoline and the like, which can shift M2-type macrophages along with further altering their phenotype into a M2 subphenotype.

In certain embodiments, the therapeutic agent is an anti-microbial drug selected from the group comprising or consisting of: an antibiotic; an anti-tuberculosis antibiotic (such as isoniazid, streptamycin, or ethambutol); an anti-viral or anti-retroviral drug, for example an inhibitor of reverse transcription (such as zidovudin) or a protease inhibitor (such as indinavir). In certain embodiments, the therapeutic agent is an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and/or zwittermicin. In certain embodiments, the therapeutic agent is selected from isoniazid, doxorubicin, dexamethasone, streptomycin, and/or tetracycline.

In some embodiments, the therapeutic agent comprises a high energy killing isotope which has the ability to kill macrophages and tissue in the surrounding macrophage environment. Suitable radioisotopes include: $^{210/212/213/214}$Bi, $^{131/140}$Ba, $^{11/14}$C, $^{51}$Cr, $^{67/68}$Ga, $^{153}$Gd, $^{99m}$Tc, $^{88/90/91}$Y, $^{123/124/125/131}$I, $^{111/115m}$In, $^{18}$F, $^{105}$Rh, $^{153}$Sm, $^{67}$Cu, $^{166}$Ho, $^{177}$Lu, $^{186/188}$Re, $^{32/33}$P, $^{46/47}$Sc, $^{72/75}$Se, $^{35}$S, $^{182}$Ta, $^{123m/127/129/132}$Te, $^{65}$Zn and $^{89/95}$Zr.

In embodiments, a therapeutic agent comprises a non-radioactive species selected from, but not limited to, the group consisting of: Bi, Ba, Mg, Ni, Au, Ag, V, Co, Pt, W, Ti, Al, Si, Os, Sn, Br, Mn, Mo, Li, Sb, F, Cr, Ga, Gd, I, Rh, Cu, Fe, P, Se, S, Zn and Zr.

In some embodiments, a therapeutic agent is selected from the group consisting of cytostatic agents, alkylating agents, antimetabolites, anti-proliferative agents, tubulin binding agents, hormones and hormone antagonists, anthracycline drugs, vinca drugs, mitomycins, bleomycins, cytotoxic nucleosides, pteridine drugs, diynenes, podophyllotoxins, toxic enzymes, and radiosensitizing drugs. By way of more specific example, the therapeutic agent is selected from the group consisting of mechlorethamine, triethylenephosphoramide, cyclophosphamide, ifosfamide, chlorambucil, busulfan, melphalan, triaziquone, nitrosourea compounds, adriamycin, carminomycin, daunorubicin (daunomycin), doxorubicin, isoniazid, indomethacin, gallium(III), 68gallium(III), aminopterin, methotrexate, methopterin, mithramycin, streptonigrin, dichloromethotrexate, mitomycin C, actinomycin-D, porfiromycin, 5-fluorouracil, floxuridine, ftorafur, 6-mercaptopurine, cytarabine, cytosine arabinoside, podophyllotoxin, etoposide, etoposide phosphate, melphalan, vinblastine, vincristine, leurosidine, vindesine, leurosine, taxol, taxane, cytochalasin B, gramicidin D, ethidium bromide, emetine, tenoposide, colchicin, dihydroxy anthracin dione, mitoxantrone, procaine, tetracaine, lidocaine, propranolol, puromycin, ricin subunit A, abrin, diptheria toxin, botulinum, cyanginosins, saxitoxin, shigatoxin, tetanus, tetrodotoxin, trichothecene, verrucologen, corticosteroids, progestins, estrogens, antiestrogens, androgens, aromatase inhibitors, calicheamicin, esperamicins, and dynemicins and combinations thereof.

In embodiments wherein the therapeutic agent is a hormone or hormone antagonist, the therapeutic agent may be selected from the group consisting of prednisone, hydroxyprogesterone, medroprogesterone, diethylstilbestrol, tamoxifen, testosterone, and aminogluthetimide and combinations thereof.

In embodiments wherein the therapeutic agent is a prodrug, the therapeutic agent may be selected from the group consisting of phosphate-containing prodrugs, thiophosphate-containing prodrugs, sulfate containing prodrugs, peptide containing prodrugs, (-lactam-containing prodrugs, optionally substituted phenoxyacetamide-containing prodrugs, optionally substituted phenylacetamide-containing prodrugs, 5-fluorocytosinem, and 5-fluorouridine prodrugs that can be converted to the more active cytotoxic free drug thereof.

Examples of constructs useful in the present invention include mannosylamino dextrans (MAD), which can comprise a dextran backbone having mannose molecules conjugated to glucose residues of the backbone and having active pharmaceutical ingredients conjugated to other glucose residues of the backbone. Tilmanocept is an example of a MAD. A tilmanocept derivative that is tilmanocept without DTPA conjugated thereto (sometimes referred to as m-tilmanocept) is a further example of a MAD. In some embodiments, the dextran-based moiety having at least one CD206 targeting moiety attached thereto can be a compound of Formula (I):

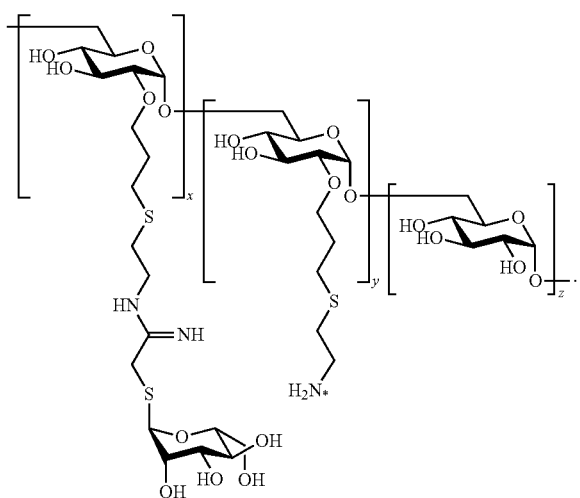

(I)

wherein the * indicates the point at which the therapeutic agent can be attached. In certain embodiments, the therapeutic agent can be attached via a linker. In certain embodiments, x can be between about 10 to about 25, about 5 to about 25, about 10 to about 20, about 15 to about 25, about 15 to about 20 and ranges therebetween. In some embodiments, y can be between about 35 and about 70, about 40 and about 70, about 50 and about 65, and ranges therebetween. In some embodiments, z can be between about 40 to about 70, about 50 to about 65, about 50 to about 60 and ranges therebetween.

In other embodiments, the compound of the present invention can be a compound of Formula (II):

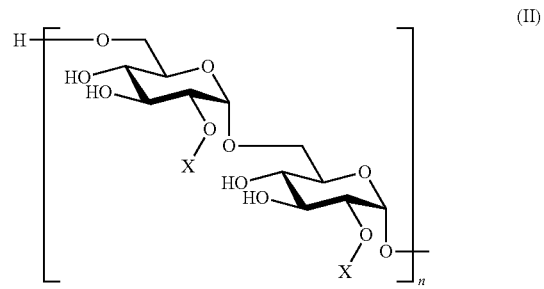

(II)

wherein
each X is independently H, $L_1$-A, or $L_2$-R; each L, and $L_2$ are independently linkers; each A independently comprises a therapeutic agent or a detection label or H;
each R independently comprises a CD206 targeting moiety or H; and
n is an integer greater than zero.

In certain embodiments, L, is a linker as described above.
In certain embodiments, $L_2$ is a linker as described above.

Synthesis

The compounds of this invention can be prepared by employing reactions as shown in the disclosed schemes provided within FIG. 6 through FIG. 9, in addition to other standard manipulations that are known in the literature, exemplified in the experimental sections or clear to one skilled in the art. The following examples are provided so that the invention might be more fully understood, are illustrative only, and should not be construed as limiting. For clarity, examples having fewer substituents can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

Figure 6:
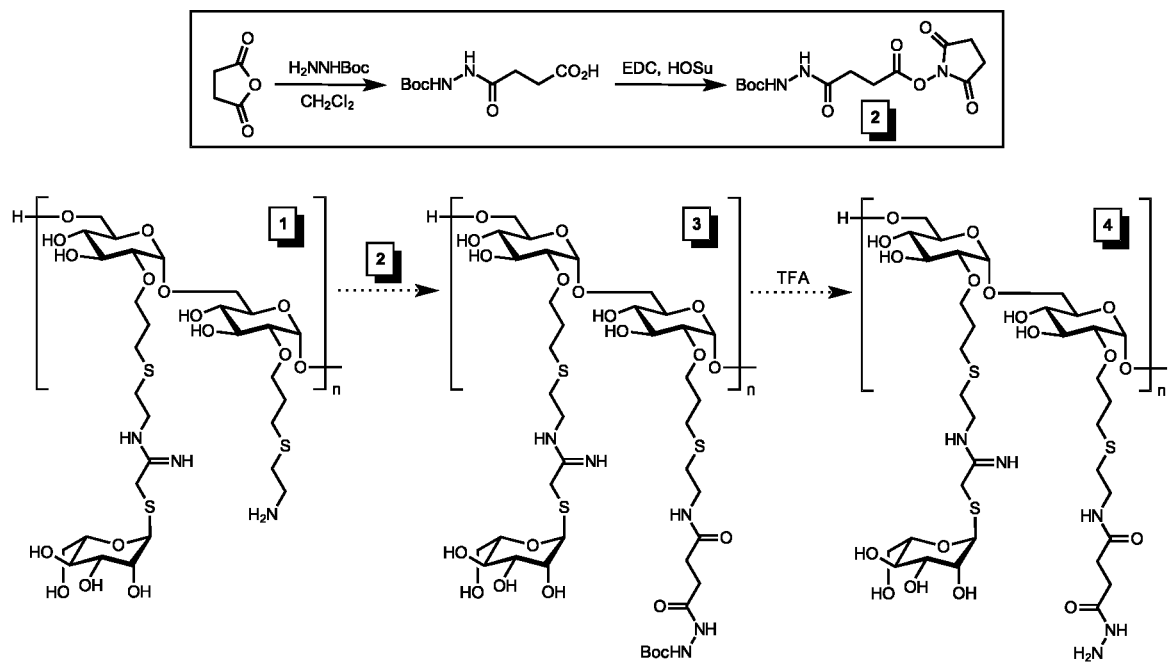
FIG. 6 shows a synthetic route (A) for the modification of a mannosylamino dextran (MAD) to form a functionalized MAD.

The compounds of the present invention may be synthesized by any number of ways known to one of ordinary skill in the art. For example, linker 2 can be synthesized by opening succinic anhydride ring by tert-butyl carbazate. The resulting carboxylic acid is converted to the corresponding N-hydroxy succinimide (NHS) ester using EDC coupling reagent. MAD is then functionalized with linker 2 by forming an amide linkage. Then, the Boc protecting group can be removed under dilute acidic condition (typically 30-40% trifluoroacetic acid in DMSO) to obtain 4, as shown in FIG. 6. Dilute acidic condition is required to avoid any unwanted cleavage of the glycosidic linkage present in dextran backbone. The resulting functionalized MAD can be purified by size exclusion filtration.

Figure 7:
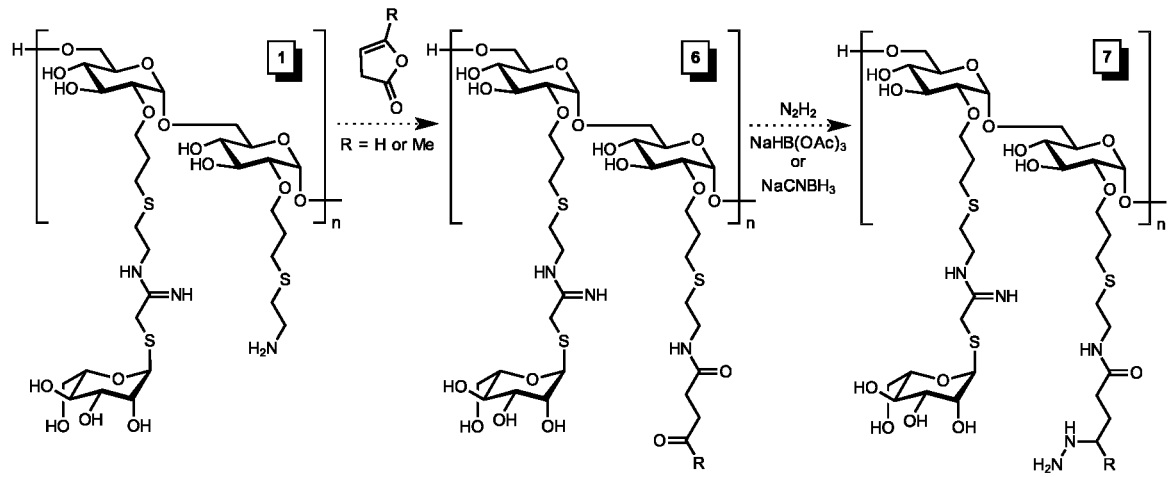
FIG. 7 shows a synthetic route (B) for the modification of a MAD to form a MAD construct with hydrazine derivative.

Alternatively, compounds according to the present invention may be synthesized according to Scheme 2 shown in FIG. 7. Free primary amine groups of MAD can be reacted with an excess of lactone under anhydrous condition. Unreacted lactone can be removed under reduced pressure to obtain modified MAD 6. The corresponding hydrazine derivative 7 can be prepared by reductive amination reaction using sodium cyanoborohydride or sodium triacetoxy borohydride as the reducing agent.

Figure 8:
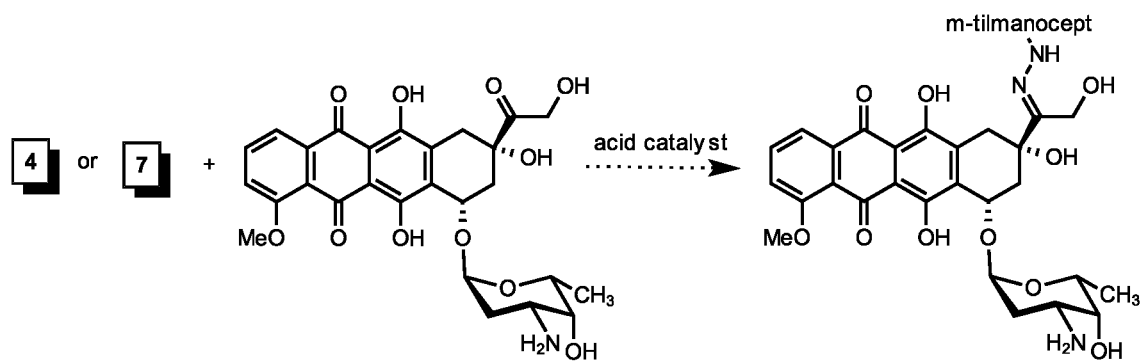
FIG. 8 shows the conjugation of oxo-containing therapeutic agents to various MAD derivatives.

The conjugation of oxo-containing therapeutic agents to MAD derivatives 4 or 7 from FIG. 6 or FIG. 7, respectively, can be as is shown in FIG. 8, under Scheme 3. MAD derivative 4 or 7 can be conjugated to doxorubicin by formation of hydrazone linkage under anhydrous acidic condition or aqueous acidic conditions. Unconjugated therapeutic agent can be removed (e.g. by size exclusion chromatography or dialyzation) to obtain the pure conjugated MAD (indicated as m-tilmanocept in FIG. 8).

Figure 9:
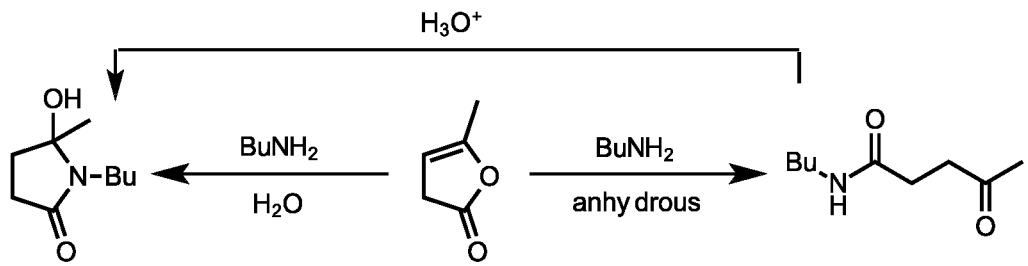
FIG. 9 shows the conjugation of amine-containing therapeutic agents to dextran-containing compounds.

Amine-containing therapeutic agents may be conjugated to dextran-containing compounds according to Scheme 4, shown in FIG. 9. The basic reaction between a primary amine and the lactone are shown in Scheme 4.

One of ordinary skill in the art would recognize other ways to synthesize the compounds of the present invention.

Pharmaceutical Compositions

Embodiments of the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier. In some embodiments, the invention relates to pharmaceutical compositions comprising a pharmaceutically acceptable carrier and an effective amount of at least one disclosed compound; or a pharmaceutically acceptable salt, hydrate, solvate, or polymorph thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In some embodiments, the pharmaceutical composition comprises a disclosed compound. In a yet further aspect, the pharmaceutical composition comprises a product of a disclosed method of making.

In some embodiments, the pharmaceutical composition is used to treat a mammal. In some embodiments, the mammal is a human. In some embodiments, the mammal has been diagnosed with a need for treatment of the disorder prior to the administering step. In some embodiments, the mammal has been identified to be in need of treatment of the disorder.

In some embodiments, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, intradermal and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids," includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as lyophilized powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

It is understood, however, that the specific dose level for any particular patient will depend upon a variety of factors and such a dosage amount would be readily ascertainable by the skilled artisan in consideration of these factors. Such factors include the age, body weight, general health, sex, and diet of the patient. Other factors include the time and route of administration, rate of excretion, drug combination, and the type and severity of the particular disease undergoing therapy.

In certain embodiments, the disclosed compounds include a detection label in addition to the therapeutic agent. As used herein, the term "detectable label or moiety" means an atom, isotope, or chemical structure which is: (1) capable of attachment to the carrier molecule; (2) nontoxic to humans or other mammalian subjects; and (3) provides a directly or indirectly detectable signal, particularly a signal which not only can be measured but whose intensity is related (e.g., proportional) to the amount of the detectable moiety. The signal may be detected by any suitable means, including spectroscopic, electrical, optical, magnetic, auditory, radio signal, or palpation detection means.

Detection labels include, but are not limited to, fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detection labels can be selected based on the choice of imaging method. For example, the detection label can be a near infrared fluorescent dye for optical imaging, a Gadolinium chelate for MRI imaging, a radionuclide for PET or SPECT imaging, or a gold nanoparticle for CT imaging.

Detection labels can be selected from, for example, a radionuclide, a radiological contrast agent, a paramagnetic ion, a metal, a fluorescent label, a chemiluminescent label, an ultrasound contrast agent, a photoactive agent, or a combination thereof. Non-limiting examples of detectable labels include a radionuclide such as $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Tc, $^{94}$Tc, $^{99m}$Tc, $^{120}$I, $^{123}$I, $^{124}$I, $^{125}$I, $^{131}$I, $^{154-158}$Gd, $^{32}$P, C, $^{13}$N, $^{15}$O, $^{186}$Re, $^{188}$Re, $^{51}$Mn, $^{52m}$Mn $^{55}$Co, $^{72}$As, $^{75}$Br, $^{76}$Br, $^{82m}$Rb, $^{83}$Sr, $^{117m}$Sn or other gamma-, beta-, or positron-emitters. Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III). Ultrasound contrast agents may comprise liposomes, such as gas-filled liposomes.

Other suitable labels include, for example, fluorescent labels (such as fluorescein, isothiocyanate, rhodamine, phycoerythrin, phycocyanin, allophycocyanin, o-phthaldehyde, and fluorescamine and fluorescent metals such as Eu or others metals from the lanthanide series), near IR dyes, quantum dots, phosphorescent labels, chemiluminescent labels or bioluminescent labels (such as luminal, isoluminol, theromatic acridinium ester, imidazole, acridinium salts, oxalate ester, dioxetane or GFP and its analogs), radioisotopes, metals, metals chelates or metallic cations or other metals or metallic cations that are particularly suited for use in in vivo, in vitro or in situ diagnosis and imaging, as well as chromophores and enzymes (such as malate dehydrogenase, staphylococcal nuclease, delta-V-steroid isomerase, yeast alcohol dehydrogenase, alpha-glycerophosphate dehydrogenase, triose phosphate isomerase, biotinavidin peroxidase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholine esterase). Other suitable labels include moieties that can be detected using NMR or ESR spectroscopy. Such labeled molecules may, for example, be used for in vitro, in vivo or in situ assays (including immunoassays known per se such as ELISA, RIA, EIA and other "sandwich assays," etc.) as well as in vivo diagnostic and imaging purposes, depending on the choice of the specific label. Another modification may involve the introduction of a chelating group, for example, to chelate one of the metals or metallic cations referred to above. Suitable chelating groups, for example, include, without limitation, diethyl-enetriaminepentaacetic acid (DTPA) or ethylenediaminetetraacetic acid (EDTA). Yet another modification may comprise the introduction of a functional group that is one part of a specific binding pair, such as the biotin-(strept) avidin binding pair. Such a functional group may be used to link a disclosed compound to a protein, polypeptide or chemical compound that is bound to the other half of the binding pair, i.e., through formation of the binding pair. For example, such a conjugated molecule may be used as a reporter, for example, in a diagnostic system where a detectable signal-producing agent is conjugated to avidin or streptavidin.

Chelating Agents

In some embodiments, a chelating agent may be attached to or incorporated into a disclosed compound, and used to chelate a therapeutic or diagnostic agent, such as a radionuclide. Exemplary chelators include but are not limited to DTPA (such as Mx-DTPA), DOTA, TETA, NETA or NOTA.

Useful chelators include, but are not limited to, DTPA, DO3A, DOTA, EDTA, TETA, EHPG, HBED, NOTA, DOTMA, TETMA, PDTA, TTHA, LICAM, HYNIC, and MECAM. HYNIC is particularly useful for chelating Tc99, another imaging agent of the invention.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

Methods of Treatment

Methods of treating or preventing diseases or disorders are provided using the disclosed compounds. The disclosed compounds can be used for targeting CD206 high expressing cells. The disclosed compounds can be used for targeting of macrophages for treatment of intracellular pathogens (*M. tuberculosis, F. tularensis, S. typhi*).

Macrophage-related and other CD206 high expressing cell-related diseases for which the compositions and methods herein may be used include, but are not limited to Leishmaniasis and other similar parasitic infections resulting in cutaneous lesions, and in particular, non-healing cutaneous lesions. Macrophage-related and other CD206 high expressing cell-related diseases for which the compositions and methods herein may be used include, but are not limited to parasitic infections, HIV, AIDS.

Tilmanocept as well as other related carrier molecules described in the '990 Patent and described herein and incorporated by reference, as well as other carrier molecules based on a dextran backbone and/or carbohydrate backbone, can bind the mannose receptor protein CD206 found on the surface of macrophages and certain other cells (e.g., Kaposi's sarcoma spindle cells) when administered to mammals or when contacted with CD206 high expressing cells ex vivo. Tilmanocept and its equivalents are discussed in PCT/US2015/041036, the entirety of which is incorporated herein by reference. CD206 is a C-type lecithin binding protein found on the surface of macrophages and certain other types of cells. The finding that the CD206 protein, found for example on the surface of macrophages, is the sole gateway for tilmanocept binding in mammalian patients means that a MAD carrier molecule (as well as related carrier molecules, such as those described herein) can be used as the basis for preparing a variety of therapeutically and diagnostically effective molecular species for use in the diagnosis and/or treatment of macrophage related diseases and other diseases mediated by CD206 high expressing cells.

Certain embodiments comprise a carrier molecule comprising a glucose-residue backbone, a CD206 targeting agent, and a therapeutic agent wherein the carrier molecule is configured to target macrophages, wherein the macrophages are dermal in an inflammatory environment resulting from Leishmaniasis infection. In certain embodiments, the CD206 targeting agent comprises mannosylated moieties. In certain embodiments, the CD206 targeting agent comprises glycosylated moieties. In certain embodiments, the CD206 targeting agent comprises a mixture of mannosylated and glycosylated moieties.

Certain embodiments may comprise a method of treatment that comprises administering a composition as described herein to M2-type macrophages. Certain embodiments specifically target M2-type macrophages. In certain embodiments these macrophages may be dermis-resident macrophages, and more particularly, M2-type dermal macrophages. Some embodiments may comprise a method that targeting M2-type macrophages for treating Leishmaniasis wherein the treatment comprises administering a composition as described herein wherein the administration comprises causing M2-type macrophage apoptosis. In some embodiments, the apoptosis is controlled to limit macrophage cell death.

The disclosed compounds can include therapeutic agents including, but not limited to, cytotoxic agents, anti-angiogenic agents, pro-apoptotic agents, antibiotics, hormones, hormone antagonists, chemokines, drugs, prodrugs, toxins, enzymes, or other agents. The disclosed compounds can include chemotherapeutic agents; antibiotics; immunological adjuvants; compounds useful for treating tuberculosis; steroids; nucleotides; peptides; or proteins.

In certain embodiments, the compounds include an antimicrobial drug selected from the group comprising or consisting of: an antibiotic; an anti-tuberculosis antibiotic (such as isoniazid, ethambutol); an anti-retroviral drug, for example an inhibitor of reverse transcription (such as zidovudin) or a protease inhibitor (such as indinavir); drugs with effect on leishmaniasis (such as Meglumine antimoniate), or any combination thereof. In certain embodiments, the compounds include an anti-microbial active, such as amoxicillin, ampicillin, tetracyclines, aminoglycosides (e.g., streptomycin), macrolides (e.g., erythromycin and its relatives), chloramphenicol, ivermectin, rifamycins and polypeptide antibiotics (e.g., polymyxin, bacitracin) and zwittermicin. In certain embodiments, the compounds include an active selected from isoniazid, doxorubicin, streptomycin, and tetracycline, or any combination thereof. The disclosed compounds can be used, for example, to treat Tuberculosis, *Staphylococcus*, *Streptococcus*, yeast, *Serratia. E. coli*, and *Pseudomonas aeruginosa* infections.

In certain embodiments, the disclosed compounds advantageously have efficacy in the treatment of a condition or disorder caused by a micro-organism, for example, a condition or disorder selected from the group comprising or consisting of: tuberculosis, AIDS; HIV infection; and Leishmaniasis, or any combination thereof.

Certain embodiments provide for methods of treating Leishmaniasis along with other anomalies, including those enumerated herein, that result in cutaneous lesions. Some embodiments can comprise administration of a compound described herein for treating cutaneous lesions caused by conditions such as those described herein, including but not limited to, Leishmaniasis. Without being bound by theory, it is believed that M2 phenotype macrophages contain a high number of CD206 receptors, thus making them particularly beneficial for specific targeting with a therapeutic agent conjugated with a carrier backbone with a CD206 targeting moiety because macrophages differentiate into M2 macrophages in the presence of *Leishmaniasis* and other conditions described herein. As a result, the present invention possesses the unexpected and superior results of treating conditions described herein, such as but not limited to Leishmaniasis, by administering a composition as described herein with an unexpectedly and superiorly high level of treatment specificity because of the identification of this phenotypical differentiation.

One of ordinary skill in the art will appreciate that various kinds of molecules and compounds (e.g., therapeutic agents, detection labels, and combinations thereof) can be delivered to a cell or tissue using the disclosed compounds.

Administration

The disclosed compounds can be administered via any suitable method. The disclosed compounds can be administered parenterally into the parenchyma or into the circulation so that the disclosed compounds reach target tissues (e.g., where cancer cells may be located). The disclosed compounds can be administered directly into or adjacent to a tumor mass. The disclosed compounds can be administered intravenously. In still other embodiments, the disclosed compounds can be administered intraperitoneally, intramuscularly, subcutaneously, intracavity, or transdermally.

Parenteral administration of the compounds, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

EXAMPLES

Example 1. Cy3-Tilmanocept Binding to Human Macrophages

Figure 1B:
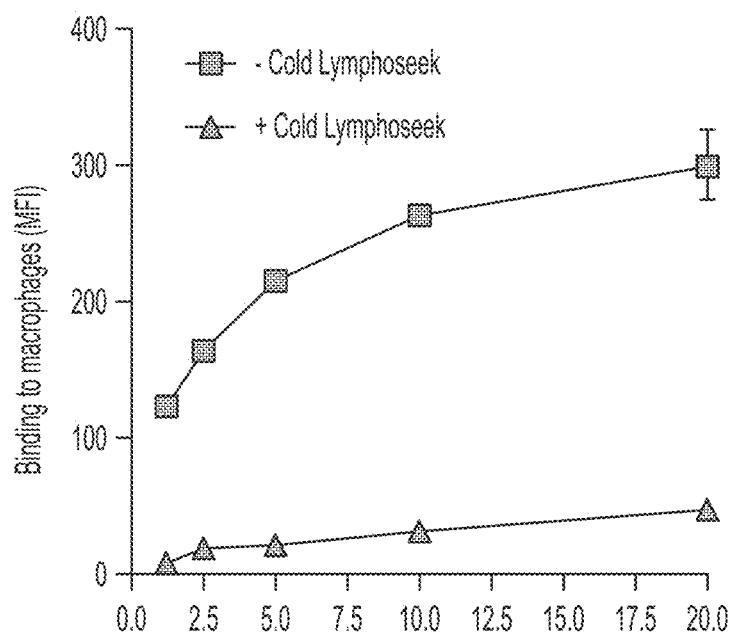

A quantity of PBMCs consisting of lymphocytes or macrophages was cultured for 5 days to enable blood monocytes to differentiate into macrophages (human monocyte-derived macrophages, or "MDMs"), and then pre-treated with or without unlabeled (cold) tilmanocept. Next, the cells were incubated with varying concentrations (1.25, 2.5, 5.0, 10 and 20 μg/mL) of Cy3-labeled tilmanocept (Cy3-tilmanocept). Binding to PBMC cell populations was analyzed by flow cytometry by gating separately for macrophages and lymphocytes. The resulting data showed that Cy3-tilmanocept binds specifically to the macrophage population in a dose-dependent manner, as shown in FIG. 1A. FIG. 1A depicts fluorescence-activated cell sorting ("FACS") analysis of PBMCs, focusing on macrophages and lymphocytes. For the macrophages that were pre-treated with cold tilmanocept (100-fold excess), the binding of Cy3-tilmanocept was nearly abolished even at the highest concentrations, as shown in FIG. 1B (FACS analysis showing inhibition of tilmanocept-Cy3 binding to macrophages in presence of unlabeled tilmanocept **P<0.005).

Figure 1C:
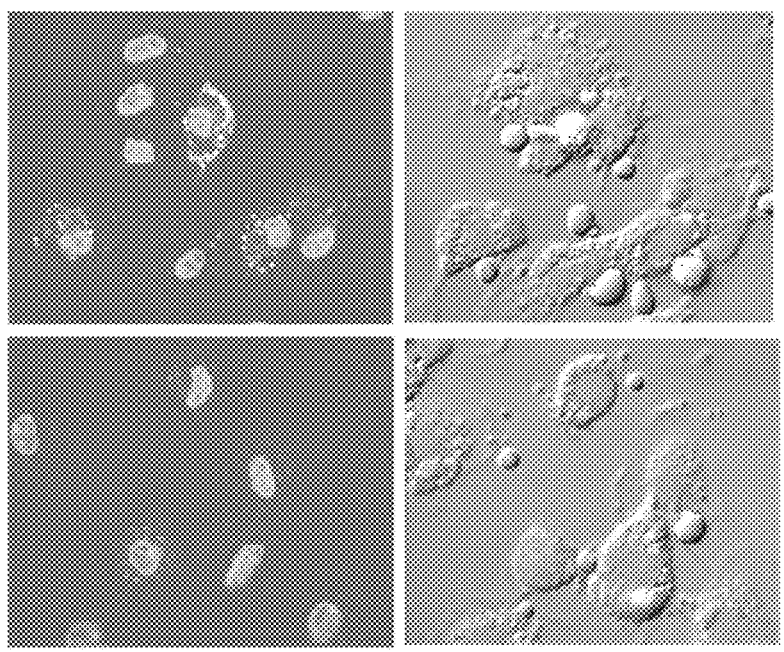

To corroborate these findings, MDMs were treated in monolayer culture in a similar way, and fluorescence confocal microscopy experiments were performed. The binding of Cy3-tilmanocept to macrophages was readily apparent and this binding was nearly abolished for macrophages that were pre-treated with cold tilmanocept, as seen in FIG. 1C. Depicted data is representative of two independent experiments, each performed in duplicate, and the results were consistent with receptor-mediated binding of Cy3-tilmanocept to macrophages. The upper and lower left images in FIG. 1C depict confocal microscopy representative images (magnification: 120×) which show binding (upper left) and inhibition of binding (lower left) of Cy3-tilmanocept to macrophages in the absence or presence of tilmanocept with no fluorophore, respectively. The gray regions indicate macrophage nuclei, and the white portions indicate Cy3-tilmanocept. The upper and lower right images in FIG. 1C are DIC images which show the individual cell structure of the adjacent fluorescent images (to the left of each DIC image). "DIC" is Differential Interference Contrast (phase contrast microscopy).

Figure 2A:
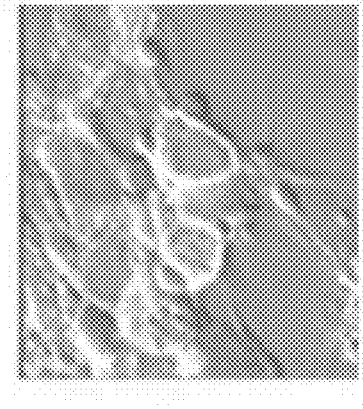
FIGS. 2A-2D show a series of images of MR206 expression and binding of an example of a macrophage-targeting compositions described herein.
Figure 2B:
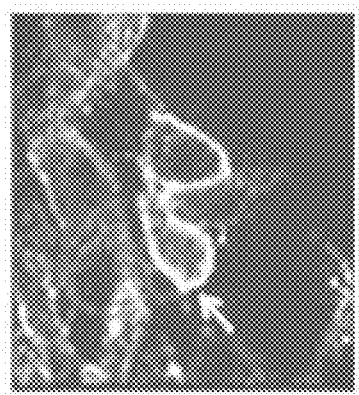
Figure 2C:
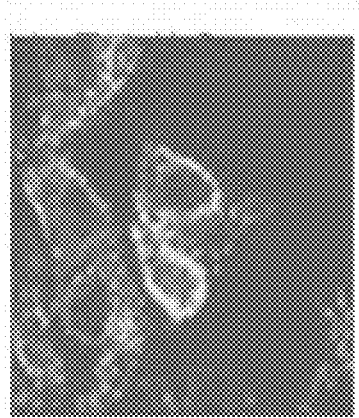
Figure 2D:
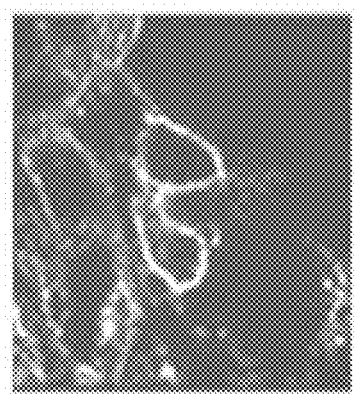

Example 2. Co-Localization of Tilmanocept with the CD206 Mannose Receptor on Human Macrophages MDM monolayers were incubated with Cy3-tilmanocept for 10 minutes, fixed with paraformaldehyde, incubated with anti-MR primary Ab, and stained with Alexa Fluor 488-conjugated secondary Ab. The monolayers were then analyzed by confocal microscopy. FIG. 2 illustrates representative confocal images (magnification: 160×) showing expression of the CD206 MR (FIG. 2A), Cy3-tilmanocept binding by the macrophage (FIG. 2B), and co-localization between the MR and Cy3-tilmanocept in both confocal and phase contrast images (FIGS. 2C and 2D). The results shown are representative of three independent experiments.

Example 3. Binding of Cy3-Tilmanocept to Macrophages Infected with Tuberculosis

Figure 3:
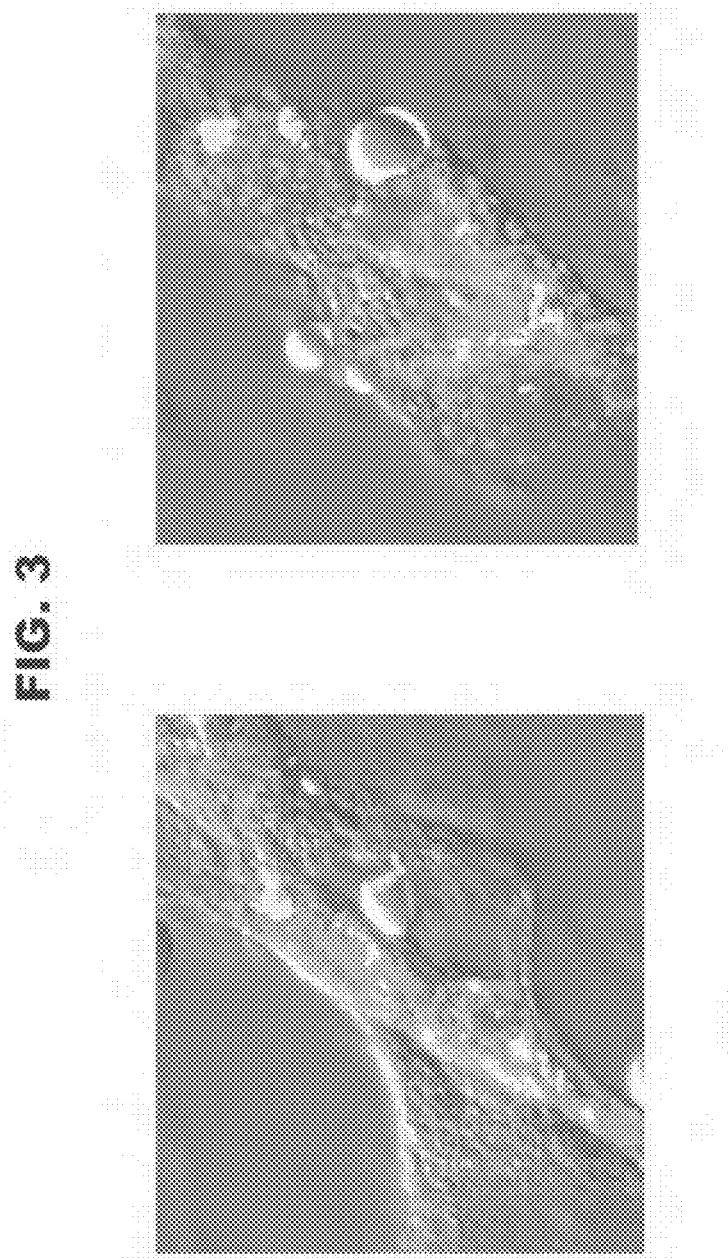
FIG. 3 shows that an example of a composition as described herein binds to, and is internalized by the macrophages.

Human monocyte-derived macrophages in monolayer culture that make up the components of the TB granulomas were infected with a GFP-expressing *M. tuberculosis* which was internalized by macrophages (GFP=green fluorescent protein). The infected cells were then exposed to Cy3-tilmanocept which had been labeled with cyanine (Cy3) dye, and analyzed by confocal microscopy. Thus, FIG. 3 demonstrates that the Cy3-tilmanocept binds to, and is internalized by the macrophages.

Figure 4:
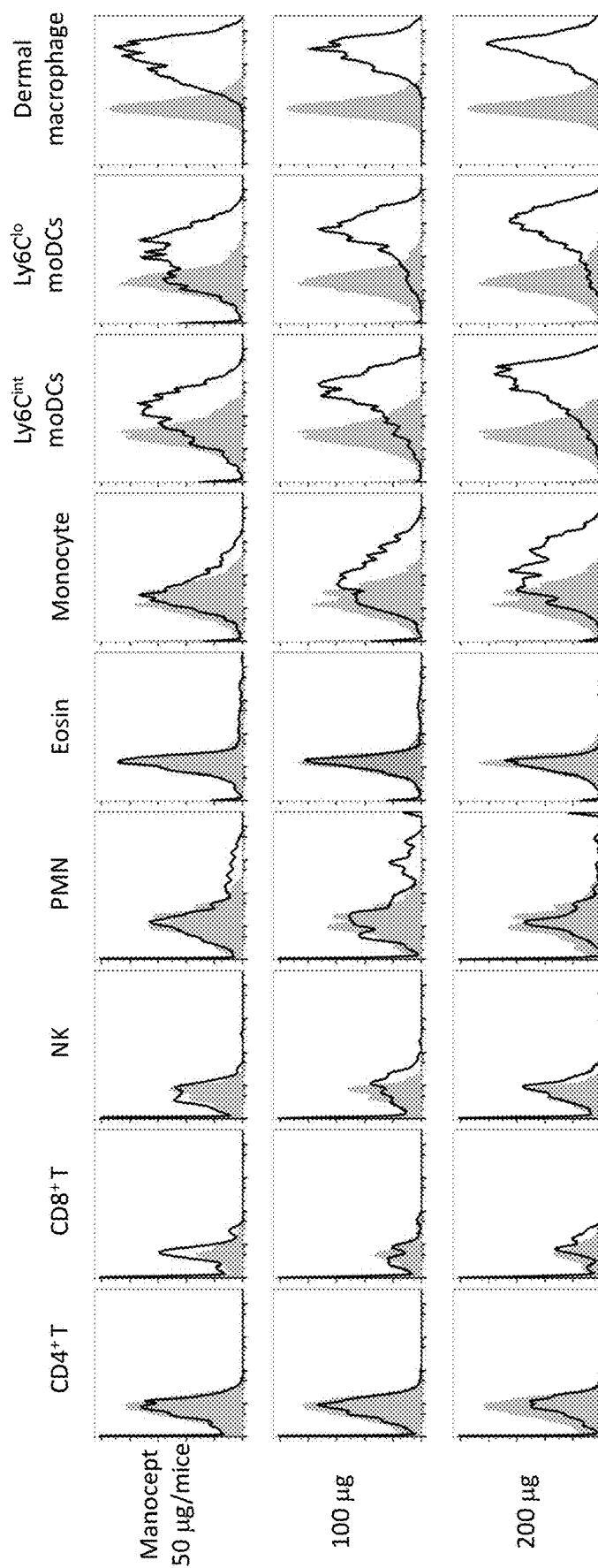
FIG. 4 shows plaque assays showing results of administration of examples compositions described herein containing therapeutic agents.
Figure 5:
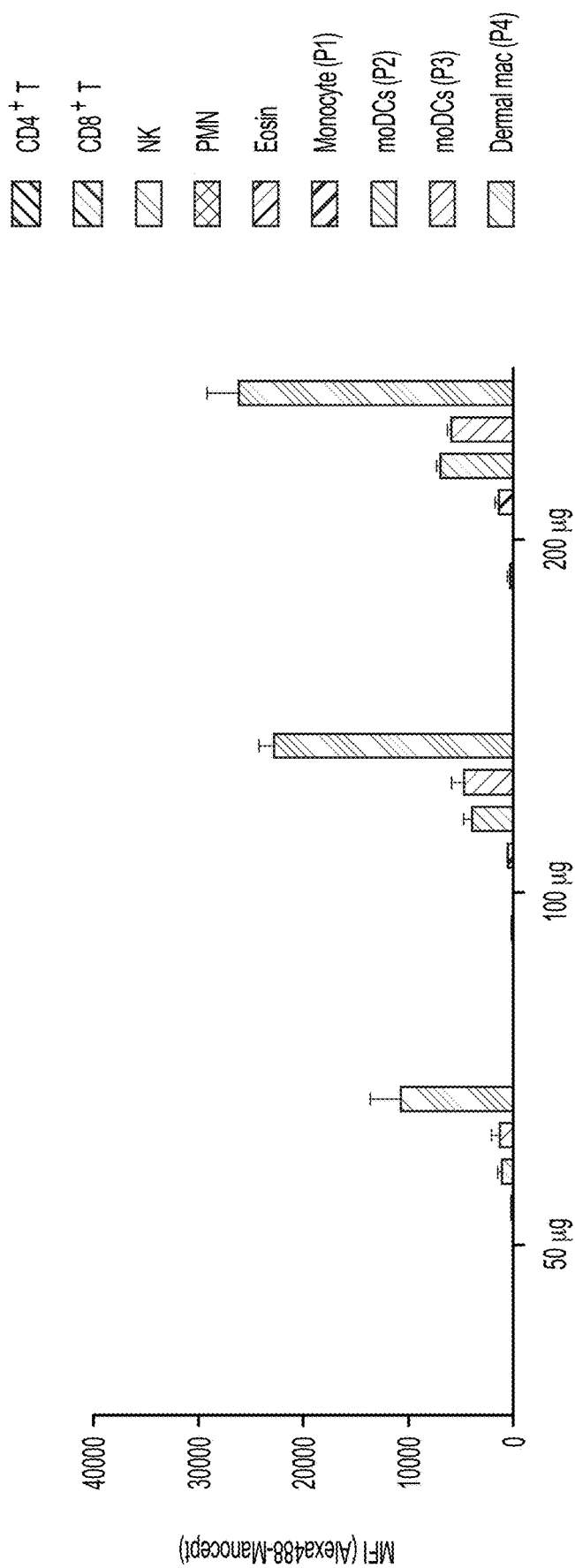
FIG. 5 shows results of administration of an example of a composition described herein to mice.

Example 4. Administration of Alexa Fluors 488-Tilmanocept to Label Mouse Dermis Resident Macrophages and Applications Related to Leishmaniasis Alexa Fluors 488-tilmanocept is introduced to ear dermis cells in vivo of nafofvC57Bl/6 mice. The Alexa Fluors 488-tilmanocept is introduced in three doses: 50 subjects with Rheumatoid arthritis. The uptake of Alexa Fluors 488-tilmanocept is then measured for CD4+T cells, CD8+T cells, natural killer (NK) cells, polymorphonuclear leukocytes (PMN), eosinophils, monocytes (PI), monocyte-derived dendritic cells (P2 and P3) and dermal macrophages (P4). The uptake of Alexa Fluors 488-tilmanocept is measured using mean fluorescence intensity (MFI) for each cell as is shown in FIG. 5. The dermal macrophages achieve an unexpectedly superior level of uptake compared to the other types of cells based on the highly selective staining results as shown by the comparative values for each injection shown in FIG. 4 and FIG. 5. The local intradermal injection of Alexa Fluors 488-tilmanocept exhibits uptake similar to intravenous introduction, which is an unexpected outcome. The amount of Alexa Fluors 488-tilmanocept taken up is highest for dermal macrophages and is unexpectedly superior at each of the injection amounts because each injection amount shows superior uptake compared to, for example, monocyte-derived dendritic cells P2 and P3 as shown in FIG. 4 and FIG. 5. This localization is unexpected and represents the leishmaniosis-specific target cells of infectivity of the protozoan.

Because the results as shown in FIG. 4 and FIG. 5 demonstrate that the cells took up negligible amounts of eosin, Alexa Fluors 488-tilmanocept also demonstrates the unexpected results that P2, P3, and P4 are highly specific in their receptor binding. Although Alexa Fluors 488-tilmanocept is used for this particular example, any of the embodiments as described herein could be substituted.

Tilmanocept will be administered to mice that have been infected with Leishmaniasis using methods known to those of skill in the art. Groups of mice will be injected with various dosage amounts up to, and including, the maximum tolerable dose. The peripheral macrophage population will then be evaluated using immunohistochemistry methods known to those of skill in the art. Tilmanocept will be administered to human patients in a double blind study. These studies include a control group receiving no treatment, groups receiving traditional treatments (e.g., administration of heavy metal poisoning using antimony and at least a second group receiving amphotericin), a group receiving tilmanocept comprising a leishmaniasis therapeutic agent, and a group receiving a placebo. The results will be measured to determine the uptake of tilmanocept along with the reduction or cure of leishmaniasis. These measurements will be based on the killing and release of protozoan products of the leishmaniosis and elimination of the clinical symptoms of the infected animals. Additionally, there may be the absence of the amastigotes from the cells within the lesions (cutaneous) and body (visceral).

Any of the embodiments of tilmanocept and its derivatives as described herein can be administered to achieve similar results.

*Leishmania* protozoan parasites (that cause leishmaniasis) live as flagellated forms in the gut of their sand fly vector but live as aflagellated forms when living in their vertebrate host. Leishmaniasis infections can cause cutaneous lesions in the vertebrate host. These lesions are susceptible to dangerous infections such as tetanus, *staphylococcus*, and *streptococcus*. The flagellated form is referred to as a promastigote and the aflagellated form is referred to as an amastigote. When feeding on a vertebrate host, a sand fly can infect the host with the promastigotes, which are then engulfed by macrophages via phagocytosis. Without being bound by theory, it is this mechanism which allows tilmanocept comprising a therapeutic agent to deliver therapeutic agents to the parasite inside the infected cells. Based on the results discovered above, tilmanocept exhibits unexpected particularity, thus allowing for improved delivery of leishmaniasis therapeutic agents to only infected macrophages while limiting the interaction that potentially toxic agents have with healthy uninfected cells in a patient.

Embodiments of tilmanocept as described herein can comprise therapeutic agents as described herein for curing, ameliorating, preventing, and/or treating leishmaniasis and/or the symptoms of leishmaniasis. In some embodiments, compositions described herein can be configured as discussed herein to specifically target Leishmania major infections. In certain embodiments where tilmanocept is used to cure, ameliorate, prevent, and/or treat leishmaniasis, the tilmanocept may comprise a therapeutic agent selected from the group consisting of amphotericin, isoniazid, heavy metal, paromomycin, miltefosine, fluconazole, pentamide, Meglumine antimoniate, and combinations thereof. In certain embodiments, tilmanocept is administered to a patient to cure, ameliorate, prevent, kill, eliminate, and/or treat amastigotes caused by leishmaniasis. In such embodiments, a therapeutic agent linked to tilmanocept can interact with an amistigote contained in an infected macrophage via the mechanisms described herein. To cure, ameliorate, prevent, and/or treat leishmaniasis, tilmanocept can be administered to a patient as described herein. In some embodiments, tilmanocept comprising a leishmaniasis therapeutic agent can be administered as a local intradermal injection. In certain embodiments, tilmanocept comprising a leishmaniasis therapeutic agent can be administered intravenously.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A method of treating leishmaniasis comprising administering to a subject in need thereof an effective amount of a compound comprising a dextran backbone having one or more CD206 targeting moieties and one or more therapeutic agents attached thereto; wherein the compound is effective for treatment of leishmaniasis disease; and wherein the compound is a compound of Formula (II):

(II)

wherein
each X is independently H, $L_1$-A, or $L_2$-R; each $L_1$ and $L_2$ are independently linkers and wherein at least one $L_1$ and at least one $L_2$ comprises a biodegradable linker;
each A independently comprises a therapeutic agent or a detection label or H; each R independently comprises a CD206 targeting moiety or H; and n is an integer greater than zero; and
wherein at least one R is a CD206 targeting moiety selected from the group consisting of mannose, fucose, and n-acetylglucosamine and at least one A is a therapeutic agent; and
wherein the compound comprises at least one $L_1$-A and at least one $L_2$-R.

2. A method of targeting tumor-associated macrophages comprising administering to a subject in need thereof an effective amount of a compound according to claim 1.

3. The method of claim 1, wherein the compound has at least one therapeutic agent and further comprising at least one detection label.

4. The method of claim 3, wherein a linker is used to attach the one or more CD206 targeting moieties, one or more therapeutic agents, and the one or more detection labels.

5. The method of claim 1, wherein the biodegradable linker of the at least one $L_1$ or the at least one $L_2$ is an acid-sensitive linker.

6. The method of claim 1, wherein at least one R is selected from the group consisting of mannose and n-acetylglucosamine.

7. The method of claim 6, wherein at least one R is mannose.

8. The method of claim 1, wherein the at least one therapeutic agent is chosen from: amphotericin, isoniazid, heavy metal, paromomycin, miltefosine, fluconazole, pentamide, Meglumine antimoniate, and combinations thereof.

9. The method of claim 1, wherein the at least one therapeutic agent is doxorubicin or dexamethasone.

10. The method of claim 1, wherein at least one A is a metal chelator bound to a metal.

11. A method of treating leishmaniasis comprising administering to a subject in need thereof an effective amount of a compound comprising a dextran backbone having one or more CD206 targeting moieties and one or more therapeutic agents attached thereto; wherein the compound is effective for treatment of leishmaniasis disease; and wherein the compound is a compound of Formula (II):

(II)

wherein
each X is independently H, $L_1$-A, or $L_2$-R; each $L_1$ and $L_2$ are independently linkers, and
wherein at least one $L_1$ and at least one $L_2$ comprises a biodegradable linker;
each A independently comprises a therapeutic agent or a detection label or H; each R independently comprises a CD206 targeting moiety or H; and
n is an integer greater than zero;
wherein the CD206 targeting moiety is mannose, and the therapeutic agent comprises doxorubicin or dexamethasone; and wherein the compound comprises at least one $L_1$-A and at least one $L_2$-R.

\* \* \* \* \*